US010052408B2

(12) United States Patent
Falcone

(10) Patent No.: US 10,052,408 B2
(45) Date of Patent: *Aug. 21, 2018

(54) COMPOSITIONS OF CARBOXYPOLYSACCHARIDES AND POLYALKYLENE OXIDES CROSS-LINKED USING POLYHYDROXYL ORGANIC ANIONS

(71) Applicant: FzioMed, Inc., San Luis Obispo, CA (US)

(72) Inventor: Samuel J. Falcone, Morro Bay, CA (US)

(73) Assignee: FZIOMED, Inc., San Luis Obispo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/818,168

(22) Filed: Nov. 20, 2017

(65) Prior Publication Data

US 2018/0071431 A1    Mar. 15, 2018

Related U.S. Application Data

(63) Continuation of application No. 15/499,112, filed on Apr. 27, 2017, now Pat. No. 9,821,088, which is a continuation of application No. 15/215,950, filed on Jul. 21, 2016, now Pat. No. 9,636,434.

(60) Provisional application No. 62/350,907, filed on Jun. 16, 2016.

(51) Int. Cl.

| C08L 1/28 | (2006.01) |
|---|---|
| A61L 27/26 | (2006.01) |
| A61L 27/50 | (2006.01) |
| A61L 27/58 | (2006.01) |
| A61L 27/52 | (2006.01) |
| A61L 31/04 | (2006.01) |
| A61L 31/14 | (2006.01) |
| C08L 71/02 | (2006.01) |

(52) U.S. Cl.
CPC ............. *A61L 27/26* (2013.01); *A61L 27/50* (2013.01); *A61L 27/52* (2013.01); *A61L 27/58* (2013.01); *A61L 31/041* (2013.01); *A61L 31/14* (2013.01); *A61L 31/145* (2013.01); *A61L 31/148* (2013.01); *C08L 1/286* (2013.01); *C08L 71/02* (2013.01); *A61L 2400/06* (2013.01); *A61L 2400/10* (2013.01); *A61L 2430/24* (2013.01); *A61L 2430/34* (2013.01); *A61L 2430/38* (2013.01); *C08L 2201/06* (2013.01); *C08L 2201/54* (2013.01); *C08L 2203/02* (2013.01); *C08L 2312/00* (2013.01)

(58) Field of Classification Search
None
See application file for complete search history.

(56) References Cited

U.S. PATENT DOCUMENTS

| 6,889,938 B1 | 3/2005 | Schwartz et al. |
| 2014/0308365 A1 | 10/2014 | Fukuda et al. |

OTHER PUBLICATIONS

BiancaGalateanu et al., Layer-shaped alginate hydrogels enhance the biological performance of human adipose-derived stem cells. BMC Biotechnology 2012, 12:35, pp. 1-14.

*Primary Examiner* — Layla D Berry
(74) *Attorney, Agent, or Firm* — D. Benjamin Borson; Borson Law Group, PC

(57) ABSTRACT

Ionically cross-linked compositions containing carboxypolysaccharides, polyalkylene oxides, polyhydroxyl organic anions, optionally divalent cations, and aqueous media are provided. Methods for manufacturing ionically cross-linked compositions of carboxypolysaccharides, polyalkylene oxides, polyhydroxyl organic anions, optionally divalent cations, and aqueous media are also provided. Such compositions can be used by placing then in proximity to a tissue in need of lubrication or for prevention of adhesions and adhesion reformation.

16 Claims, 4 Drawing Sheets

COMPOSITIONS OF CARBOXYPOLYSACCHARIDES AND POLYALKYLENE OXIDES CROSS-LINKED USING POLYHYDROXYL ORGANIC ANIONS

CLAIM OF PRIORITY

This Continuation application claims priority to U.S. patent application Ser. No. 15/499,112 filed 27 Apr. 2017, (now U.S. Pat. No. 9,821,088 issued 21 Nov. 2017), which is a Continuation of U.S. patent application Ser. No. 15/215,950 filed 21 Jul. 2016 (now U.S. Pat. No. 9,636,434, issued 2 May 2017), which claims priority to U.S. Provisional Application No. 62/350,907 filed 16 Jun. 2016 entitled "Compositions of Carboxymethylcellulose and Polyethylene Oxide Cross-Linked Using Polyhydroxyl Organic Anions, Samuel J. Falcone, Inventor. The above patents and applications are incorporated herein fully by reference.

FIELD OF THE DISCLOSURE

This disclosure relates generally to the manufacture and use of compositions comprising polyacids, polyalkylene oxides, and polyhydroxyl organic anions to form intermacromolecular complexes. Particularly, this disclosure relates to cross-linked compositions comprising carboxypolysaccharides, polyethers, and polyhydroxyl organic anions and the use of those compositions.

BACKGROUND

Carboxymethylcellulose (CMC) is a water soluble, biocompatible and bioresorbable semi-synthesized polysaccharide. The safety of commercially available CMC having high purity has been identified and approved by the Food and Drug Administration (FDA) for incorporation into many products. CMC is able to react with various polymers by way of electrostatic interaction, ionic cross-linking, hydrogen bonding, Van der Waals interactions, and physical interpenetration. Because of its safety, convenience and diversity of physico-chemical properties, CMC has demonstrated applications in the pharmaceutical, food and cosmetic industries.

CMC is one type of carboxypolysaccharide (CPS). CPSs have also been used in the manufacture of implantable polymers. CPSs are polymers made of saccharide monomers in which some of the hydroxyl (—OH) groups are replaced with carboxyl groups (—COOH or COO—). Thus, CPSs such as CMC have some hydroxyl groups and some carboxyl groups present. Carboxylation can permit ionic interaction within a polymer chain or can permit interaction between polymer chains, thereby forming a gel. Such gels have been used for a variety of applications, including implantable medical polymers.

Polyethers (PE) are polymers made of chains of ether residues (—CH$_2$—CH$_2$—). Polyethylene Oxide (PEO) is a polymer made with PE having hydroxyl groups. PEOs can therefore form hydrogen bonds with carboxyl groups on CPSs, thereby forming a hydrogen-bonded composition. More generally, polyalkylene oxides (POs or PAOs) can react in similar fashions with CPSs to form hydrogen bonded cross-linked compositions.

Adhesions are unwanted tissue growths occurring between layers of adjacent bodily tissue or between tissues and internal organs. Adhesions commonly form during the healing which follows surgical procedures, and when present, adhesions can prevent the normal motions of those tissues and organs with respect to their neighboring structures.

The medical and scientific communities have studied ways of reducing the formation of post-surgical adhesions by the use of high molecular weight carboxyl-containing biopolymers. These biopolymers can act as physical barriers to separate tissues from each other during healing, so that adhesions between normally adjacent structures do not form.

SUMMARY

We have identified a new problem in the field, namely the need and desire to provide ionically cross-linked biocompatible compositions having improved viscoelastic properties without increasing the body's burden for eliminating the high molecular weight components of such compositions. Thus, there are several objects of the instant disclosure.

One object is to provide compositions and methods for manufacture and use of CPS/PO/compositions cross-linked with polyhydroxyl organic anions.

One object is to provide compositions and methods which can be used to reduce the incidence of adhesion formation during and after surgery. This includes the prevention of de novo adhesion formation in primary or secondary surgery.

One object is to prevent reformation of adhesions after a secondary procedure intended to eliminate the de novo adhesions which had formed after a primary procedure.

One object is to provide antiadhesion compositions which remain at the surgical site during the initial stages of critical wound healing.

One object of the disclosure is to provide antiadhesion compositions which can hydrate quickly in a controlled fashion.

One object of the disclosure is to provide compositions with desired properties with incorporated drugs, so that the drug can be delivered locally over a period of time to the surgical site.

One object of the disclosure is to provide compositions having improved viscoelastic, antiadhesion, coatability, tissue adherence, anti-thrombogenicity or bioresorbability.

To achieve these and other objectives, in embodiments of the instant disclosure one can carefully control the properties of antiadhesion compositions by closely regulating the pH, amounts of carboxyl residues, polyether, cations, and polyhydroxyl anions within the carboxypolysaccharide/polyether association complex, to closely control the degree of association between the polymers using polyhydroxyl organic anions.

In embodiments, polyhydroxyl organic anions such as gluconate can be used to provide intermolecular attraction, thereby providing compositions having increased viscosity, and provide composition viscosity control, compared to those made with CPS and PEO alone.

Creation of complexes in the form of compositions with desired properties is accomplished by varying the degree of hydrogen bonding between the polymers. This variation in properties is accomplished by varying the amount of polyhydroxyl organic anion in the composition, the pH of the composition, the molecular weights of the polymers, the percentage composition of the polymer mixture, and/or the degree of substitution (d.s.) by carboxyl residues within the CMC or CPS, and the presence and concentration(s) of polyhydroxyl anions.

To address the problems of the prior art antiadhesion compositions, we have discovered new compositions based on association complexation between ionically associated carboxymethylcellulose (CMC) and hydrophilic polyethylene oxides (PEO). Cross-linked compositions of this disclosure can be made by dissolving CMC and PEO as dry powders in an aqueous solution, containing polyhydroxyl anions, and optionally multivalent cations to provide cross-linking between the CMC and the PEO with the polyhydroxyl organic anions acting as bridges for hydrogen bonding or van Der Waals interactions.

In embodiments of the disclosure, poly hydroxyl organic anions such as gluconate, and optionally, multivalent cations including $Ca^{2+}$ can be used to provide intermolecular attraction, thereby providing compositions having increased viscosity and provide viscosity control of the composition.

We unexpectedly found that CPS/PO gels made using poly hydroxyl organic anions exhibited viscoelastic properties very different from CPS/PO gels made with calcium chloride. In particular, we found that gels made using calcium chloride exhibited decreased viscosity with increasing concentration of calcium chloride. In striking contrast, similar CPS/PO gels made with polyhydroxyl organic anions exhibited increased viscosity at the same calcium ion concentration compared to gels made with calcium chloride. We further found, quite unexpectedly, that with increasing concentration of polyhydroxyl organic anions, the viscosity of CPS/PO gels increased with increasing calcium concentration. The increased viscosity and increasing viscosity with increasing calcium concentration of CPS/PO gels made with calcium/polyhydroxyl organic anions was completely unexpected based on the prior art.

The compositions of this disclosure can be used to inhibit post-surgical adhesions, to decrease the consequences of arthritis or other disorders of joints, and/or to provide a lubricant for numerous medical and/or veterinary uses.

Additionally, in accordance with some aspects of the disclosure, drugs can be included in the compositions to deliver pharmacological compounds directly to the tissues.

In certain embodiments, the compositions can be sterilized using thermal methods, gamma irradiation, and ion beams which can alter the physical and other properties of the components. Alternatively, in other embodiments of this invention, the materials can be filter sterilized.

Manufacture of such compositions in the forms of membranes, beads, particulates, coatings and gels and some of their uses has been described in U.S. Pat. Nos. 5,096,997, 6,017,301, 6,034,140, 6,133,325, 6,566,345, 6,869,938 and 7.192,984, each patent expressly incorporated herein fully by reference as if individually so incorporated.

Compositions of this invention can be useful for delivering drugs to tissues. The sites of delivery of drugs using the compositions of this invention include, without limitation, skin, wounds, mucosa, internal organs, endothelium, mesothelium, epithelium. In certain embodiments, buccal, optical, nasal, intestinal, anal, vaginal applications using compositions of this invention can be used.

BRIEF DESCRIPTION OF THE FIGURES

The invention will be described with respect to the particular embodiments thereof. Other objects, features, and advantages of the invention will become apparent with reference to the specification and drawings in which.

DETAILED DESCRIPTION

Definitions

Figure 1:
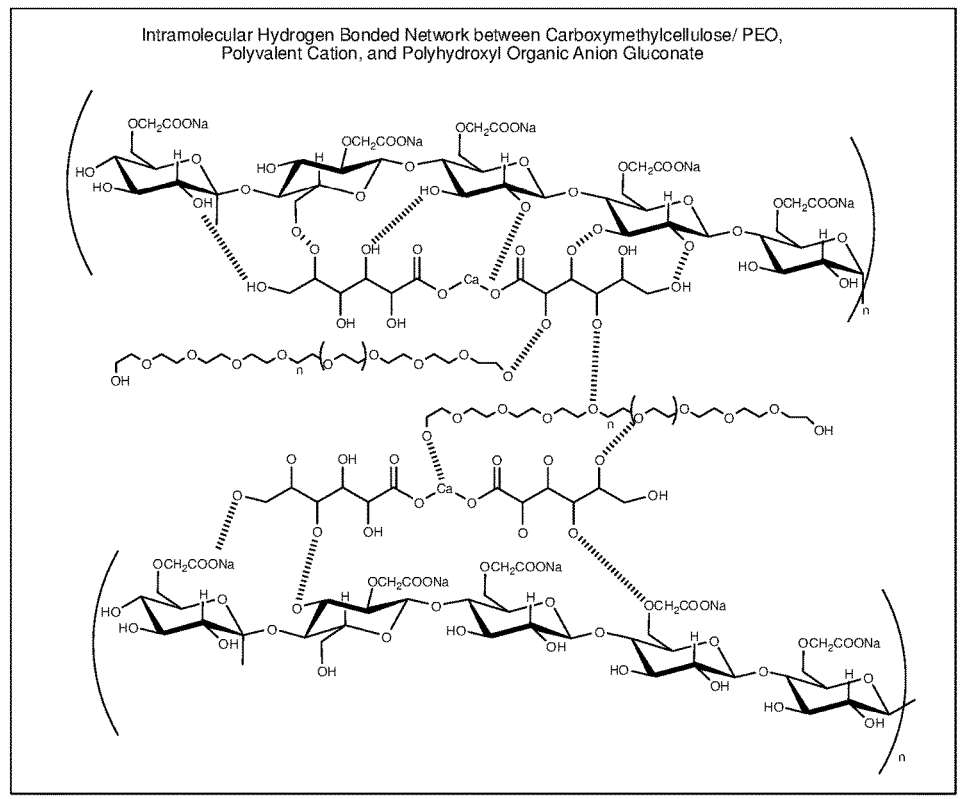
FIG. 1 depicts a chemical diagram showing CMC and PEO polymers cross-linked with and gluconate. The portion of CMC shown includes two cellobiose units (each CMAG Unit having a FW of 242 Daltons).

The following definitions apply in general to the descriptions that follow. In certain cases, however, a term may be defined differently. In those cases, the proper definition will be provided.

The term "cross-linking" or "crosslinking" means covalent bonding of two polymer chains together using a chemical reagent.

The term "carboxypolysaccharide" (CPS) means a polymer composed of repeating units of one or more monosaccharides, and wherein at least one of the monosaccharide units has a hydroxyl residue substituted with a carboxyl residue.

The term "CMC" means sodium carboxymethylcellulose. "CMC A" is Hercules CMC grade 7H PH. and "CMC B" is Hercules grade 9M31F PH. PEO A is of average molecular weight of 8000 Daltons and PEO B is of average molecular weight 4.4M Daltons.

The term "comprising" and "comprises" means includes enumerated components but is not limited to those components, and may include additional components.

The term "consisting of" means includes the enumerated components and is limited to those components.

The term "consisting essentially of" means includes the enumerated components and their equivalents.

The term "polyalkylene oxide" ("PO" or "PAO") means non-ionic polymers comprising alkylene oxide monomers. Examples of polyalkylene oxides include polyethylene oxide (PEO), polypropylene oxide (PPO) and polyethylene glycol (PEG), or block copolymers comprising PO and/or PPO.

The term "Polyethylene Oxide" ("PEO") means the non-ionic polyether polymer composed of ethylene oxide monomers The molecular weight of PEO as used herein is between 5,000 Daltons ("D") and 8,000 kiloDaltons ("kD").

The term "polyethylene glycol" ("PEG") means a non-ionic polyether polymer being composed of ethylene oxide monomers, and having a molecular weight in the range of about 200 Daltons ("D") to about 5000 Daltons.

The term "Dalton" or "D" means a unit of molecular mass, where one D is equivalent to the mass of a proton.

The term "PEG" or "polyethylene glycol" means a polymer made of repeating units of compounds containing —(O—CH$_2$—CH$_2$)— but having molecular weights in the range of about 200 Daltons to about 5000 kDa.

The term "hydrogel" means a polymer matrix that swells in water but does not dissolve in water.

The term "transmural pressure" means the hydrostatic pressure inside the sac minus the hydrostatic pressure outside the sac.

The term "Laplace's laws" refer to two relationships between transmural pressure, radius of a containment device (e.g., a "bag" or a "sac") and the wall stress. For a sphere, the wall tension "T"=Pressure "P" times Radius "R," or T=PR. For a cylinder, T=PR/2.

The term "viscosity" refers to a liquid-like property of a material having a relatively high resistance to flow in response to an applied force. Viscosity is a measure of the viscous, or liquid-like, nature of the material.

The term "Storage Viscosity" (G'/ω) is the elastic modulus G' divided by the frequency (w), The term "Dynamic Viscosity" (G"/ω) is the loss modulus (G") divided by the frequency (w).

The term "viscoelastic" means a property of polymeric materials that have both elastic (solid-like) and viscous (liquid-like) properties.

The term "elasticity" means a rheological property defined as the contribution of the elastic modulus, G', to the overall stiffness of the material. Elasticity includes Percent Elasticity as a specific example.

The term "Percent Elasticity" is defined as to be equal to: 100*G'/(G'+G").

The term "pseudoplastic" means a rheological property of some polymer solutions characterized by a decrease in solution viscosity at increasing shear rates.

The term "thixotropy" means a rheological property of some polymer solutions characterized by a time-dependent decrease in solution viscosity at a constant shear.

The term "Fourier Transform Infrared Spectroscopy," "FTIR Spectroscopy" or "FTIR" means an analytical technique that is used to detect various organic functional groups such as esters, ethers, etc. FTIR is based on absorbance of infrared electromagnetic radiation by molecules (such as functional groups).

The term "carboxymethyl anhydroglucose unit" or "CMAG unit" or "CMAG" is an individual repeat unit of a polysaccharide polymer chain.

The term "phosphate buffered saline" or "PBS" means a solution of water containing a phosphate buffer.

The term "ionic cross-linking" or "ionic crosslinking" is a method of combining constituents through ionic bonds.

The term "physiological compatible aqueous solution" means a water-based solution containing other components rendering the solution able to be introduced into a body without causing deleterious effects. Physiologically compatible aqueous solutions may have similar osmolarity (osmolality) as a body, may have a pH in the range of about 5.0 to about 8.0.

The terms "% by weight" of a CPS or CPS/PO composition means a certain weight of the dry component dissolved in a certain weight of solvent. For example, a 10% solution by weight includes 10 grams (gms) of a CPS dissolved in 100 gms of solvent.

The term "% weight per volume" means a certain weight of dry component dissolved in a solution having a total of a certain final volume. For example, a 10% weight/volume solution is one having 10 grams of solute as part of 100 ml of solution.

Advantages of the Disclosure

Embodiments of the instant disclosure have significant advantages over prior art compositions. For example, Balazs et al., U.S. Pat. No. 4,141,973 discloses the use of a hyaluronic acid (HA) fraction for the prevention of adhesions. However, because HA is relatively soluble and readily degraded in vivo, it has a relatively short half-life in vivo of 1 to 3 days, which limits its efficacy as an adhesion preventative.

Methyl cellulose and methyl cellulose derivatives are also known to reduce the formation of adhesions and scarring that may develop following surgery. (Thomas E. Elkins, et al., *Adhesion Prevention by Solutions of Sodium Carboxymethylcellulose in the Rat, Part I, Fertility and Sterility*, Vol. 41, No. 6, June 1984; Thomas E. Elkins, M. D. et al., *Adhesion Prevention by Solutions of Sodium Carboxymethylcellulose in the Rat, Part II, Fertility and Sterility*, Vol. 41. No. 6, June 1984. However, these solutions are rapidly reabsorbed by the body and disappear from the surgical site.

Additionally, solutions of polyethers can also decrease the incidence of post-surgical adhesions. Pennell et al., U.S. Pat. No. 4,993,585 describes the use of polyethylene oxide in solutions of up to 15% to decrease formation of post-surgical adhesions. Pennell et al., U.S. Pat. No. 5,156,839 describes the use of mixtures of carboxymethylcellulose up to about 2.5% by weight, and polyethylene oxide, in concentrations of up to about 0.5% by weight in physiologically acceptable, pH neutral mixtures. Because of the neutral pH, these materials do not form association complexes, and thus, being soluble, are cleared from the body within a short period of time.

The above-described solutions can have disadvantages in that they can have short biological residence times and therefore may not remain at the site of repair for sufficiently long times to have the desired anti-adhesion effects. Therefore, antiadhesion membranes using certain polymers have been made.

Although certain carboxypolysaccharide-containing membranes have been described, prior membranes can have disadvantages for use to prevent adhesions under certain conditions. Butler, U.S. Pat. No. 3,064,313 describes the manufacture of films made of 100% carboxymethylcellulose (CMC) with a degree of substitution of 0.5 and below, made insoluble by acidifying the solution to pH of between 3 and 5, and then drying the mixture at 70EC to create a film. These films were not designed to be used as anti-adhesion barriers.

Anderson, U.S. Pat. No. 3,328,259 describes making films of 100% carboxymethylcellulose and polyethylene oxide, alkali metal salts, and a plasticizing agent for use as external bandages. These materials are rapidly soluble in plasma and water and thus would have a very short residence time as an intact film. Therefore, these compositions are not suitable for alleviating surgical adhesions.

Smith et al., U.S. Pat. No. 3,387,061 describes insoluble association complexes of carboxymethylcellulose and polyethylene oxide made by lowering the pH to below 3.5 and preferably below 3.0, and then drying and baking the resulting precipitate (see Example XXXVIII). These membranes were not designed for surgical use to alleviate adhesions. Such membranes are too insoluble, too stiff, and swell to little to be ideal for preventing post-surgical adhesions.

Burns et al., U.S. Pat. No. 5,017,229 describes water insoluble films made of hyaluronic acid, carboxymethyl cellulose, and a chemical cross-linking agent. Because of the covalent cross-linking with a carbodiimide, these films need extensive cleaning procedures to get rid of the excess cross-linking agent; and because they are made without a plasticizer, they are too stiff and brittle to be ideally suited for preventing adhesions—they do not readily conform to the shapes of tissues and organs of the body.

Thus, there is a need for antiadhesion compositions that can be used under a variety of different circumstances. D.

Wiseman reviews the state of the art of the field in *Polymers for the Prevention of Surgical Adhesions, In: Polymeric Site-specific Pharmacotherapy*, A. J. Domb, Ed., Wiley & Sons, (1994). A currently available antiadhesion gel is made of ionically cross-linked hyaluronic acid. (Huang et al., U.S. Pat. No. 5,532,221).

Ionic cross-linking of polysaccharides is well documented in the chemical and patent literature (Morris and Norton, *Polysaccharide Aggregation in Solutions and Gels*, Ch. 19, in *Aggregation Processes in Solution*, Wyn-Jones, E. and Gormally, J, Eds., Elsevier Sci. Publ. Co. NY (1983)). Each type of metal ion can be used to form gels of different polymers under specific conditions of pH, ionic strength, ion concentration and concentrations of polymeric components. For example, alginate (a linear 1,4-linked beta-D-mannuronic acid, alpha-L-glucuronic acid polysaccharide) can form association structures between polyglucuronate sequences in which divalent calcium ions can bind, leading to ordered structures and gel formation. Similar calcium binding ability is also demonstrated by pectin which has a poly-D-galacturonate sequence. The order of selectivity of cations for pectins is $Ba^{2+} > Sr^{2+} > Ca^{2+}$. CMC also can bind to monovalent and divalent cations, and CMC solutions can gel with the addition of certain trivalent cations (*Cellulose Gum*, Hercules, Inc., page 23 (1984)).

Sayce et al. (U.S. Pat. No. 3,969,290) discloses an air freshener gel comprising CMC and trivalent cations such as chromium or aluminum.

Smith (U.S. Pat. No. 3,757,786) describes synthetic surgical sutures made from water-insoluble metal salts of cellulose ethers.

Shimizu et al. (U.S. Pat. No. 4,024,073) describe hydrogels consisting of water-soluble polymers such as dextran and starch chelated with cystine or lysine through polyvalent cations.

Mason et al. (U.S. Pat. No. 4,121,719) disclose CMC- and gum arabic-aluminum hydrogels used as phosphate binding agents in the treatment of hyperphosphatemia.

U.S. Pat. No. 5,266,326 describes alginate gels made insoluble by calcium chloride.

An antiadhesion gel is made of ionically cross-linked hyaluronic acid (Huang et al., U.S. Pat. No. 5,532,221). Cross-linking is created by the inclusion of polyvalent cations, such as ferric, aluminum or chromium salts. Hyaluronic acid (either from natural sources or bio-engineered) is quite expensive.

Pennell et al (U.S. Pat. No. 5,156,839) describes CMC solutions containing small amounts of high molecular weight PEO. In one embodiment, Pennell describes covalently cross-linking gels using dimethylolurea.

Schwartz et al. (U.S. Pat. Nos. 5,906,997, 6,017,301, 6,034,140, and 6,133,325) describe compositions of carboxypolysaccharide polyether complexes and their use in reducing surgical adhesions.

Schwartz et al (U.S. Pat. No. 6,869,938) describes compositions of polyacids and polyalkylene oxides ionically cross-linked with calcium chloride for reducing adhesions.

Berg et al. (U.S. Pat. No. 7,192,984) describes compositions of polyacids and polyethers as dermal fillers.

Falcone et al. (U.S. Pat. Nos. 9,161,987, 9,345,809 and U.S. patent application Ser. No. 14/887,717) describe compositions of covalently crosslinked CMC/PEG and medical uses.

Therefore, the prior art discloses no compositions which are ideally suited to the variety of uses of the instant disclosure.

Descriptions of Specific Embodiments

The descriptions of specific embodiments is intended to illustrate aspects of this disclosure, and is not intended to limit the scope of this disclosure. It can be appreciated that other applications of the compositions described herein can be developed by persons of ordinary skill in the art without undue experimentation. All of those embodiments are considered part of this disclosure.

CPS/PO Compositions

This disclosure includes a variety of compositions having CPSs and POs, linked with polyhydroxyl organic anions and optionally multivalent cations. For example, CMCs are polymers composed of sugar residues linked together, and one or more of which may have a carboxyl residue attached to the sugar moiety. There are three (3) potential sites for carboxylation on each sugar residue of CMC. Because a carboxyl residue can be chemically reactive, those locations on CMC are potential sites for derivatization. By controlling the degree of substitution ("DS" or "ds") of the CMC or CPS, the number of active groups on the derivatized CMC can be controlled.

FIG. 1 depicts a chemical diagram showing CMC and PEO polymers cross-linked with and gluconate. The portion of CMC shown includes two cellobiose units (each CMAG Unit having a FW of 242 Daltons).

Figure 2:
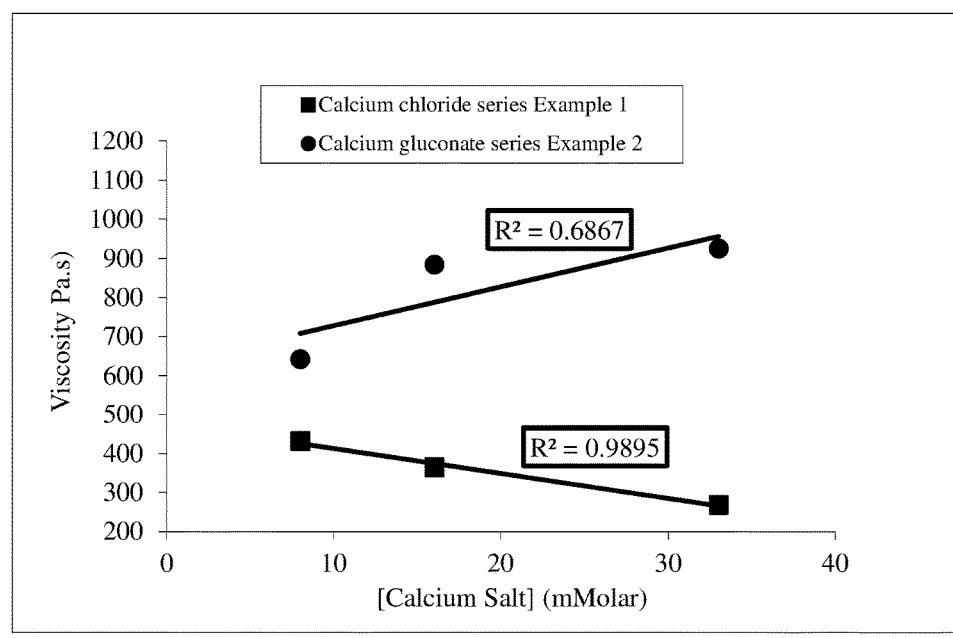
FIG. 2 depicts graphs of viscosity (in Pascal·sec. "Pa·s"; vertical axis) of CMC/PEO gels made with either calcium chloride (lower graph; filled squares) or calcium gluconate (upper graph; filled circles) at different calcium concentrations (horizontal axis) as described in Examples 1 and 2.

FIG. 2 depicts graphs of viscosity (in Pascal·sec. "Pa·s"; vertical axis) of CMC/PEO gels made with either calcium chloride (lower graph; filled squares) or calcium gluconate (upper graph; filled circles) at different calcium concentrations (horizontal axis) as described in Examples 1 and 2.

Figure 3:
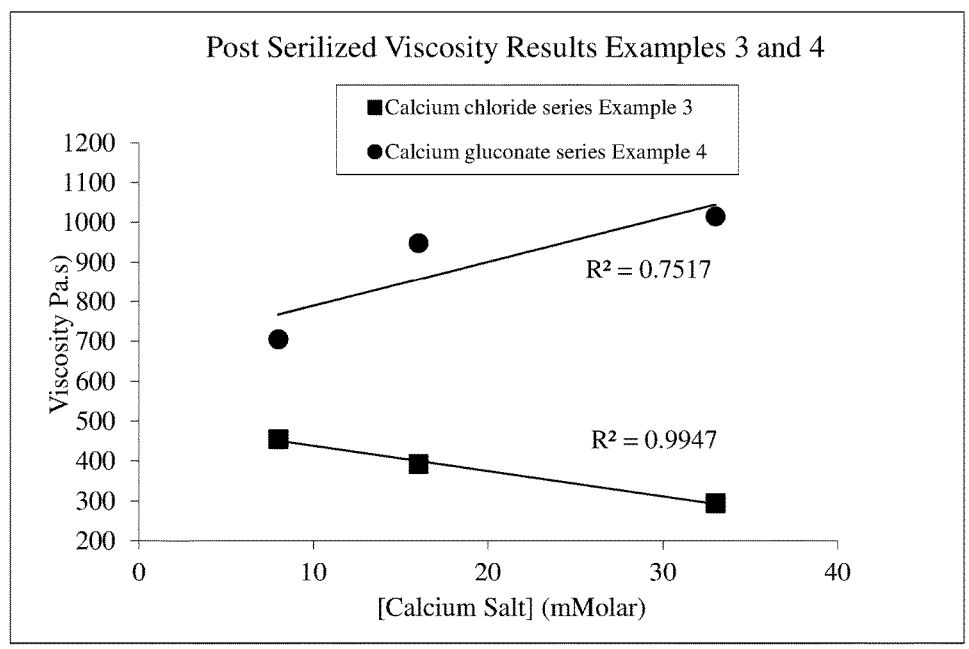
FIG. 3 depicts graphs of viscosity (in Pascal·sec. "Pa·s"; vertical axis) of CMC/PEO gels made with either calcium chloride (lower graph; filled squares) or calcium gluconate (upper graph; filled circles) at different calcium concentrations (horizontal axis) as described in Examples 3 and 4.

FIG. 3 depicts graphs of viscosity (in Pascal·sec. "Pa·s"; vertical axis) of CMC/PEO gels made with either calcium chloride (lower graph; filled squares) or calcium gluconate (upper graph; filled circles) at different calcium concentrations (horizontal axis) as described in Examples 3 and 4.

Figure 4:
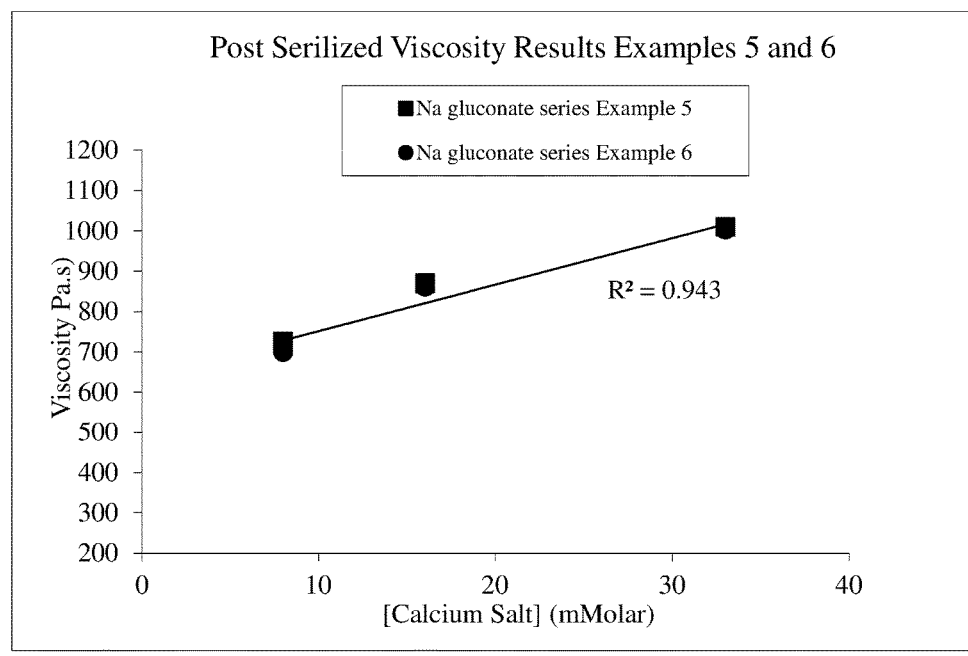
FIG. 4 depicts graphs of viscosity (in Pascal·sec. "Pa·s"; vertical axis) of CMC/PEO gels made with sodium gluconate (upper graph; filled circles) at different calcium concentrations (horizontal axis) as described in Examples 5 and 6.

FIG. 4 depicts graphs of viscosity (in Pascal·sec. "Pa·s"; vertical axis) of CMC/PEO gels made with sodium gluconate (upper graph; filled circles) at different calcium concentrations (horizontal axis) as described in Examples 5 and 6.

Preparation of CPS/PO Ionically-Crosslinked Compositions

The CPS/PO compositions of this disclosure can be prepared into one or more of several forms, including gels, membranes, beads, sponges and coatings.

The types of CPSs that can be included in this disclosure are not limited to CMC. Rather, carboxyethyl cellulose (CEC), hydroxymethyl cellulose (HMC), cellulose and other cellulose derivatives can be used.

Uses of CPS/PO Compositions

CPS/PO compositions of this disclosure can be used for one or more of the following:

(1) as space filling materials, including those suitable for implantation as load-bearing compositions placed at locations where compressive loads may occur, such as in the spinal cord, for augmentation or replacement of the nucleus pulposus;

(2) as delivery vehicles for controlled release of bioactive substances, such as drugs, growth factors, active peptides, genes, cells, clotting factors such as thrombin, and antibiotics hormones including epinephrine, steroids, anti-inflammatory agents and the like, and vasoconstrictors such as norepinephine and the like;

(3) as delivery vehicles for the localized release of bioactive substances, such as drugs, growth factors, active peptides, genes, cells, clotting factors such as thrombin, and antibiotics, hormones including epinephrine, steroids, anti-inflammatory agents and the like, and vasoconstrictors such as norepinephrine and the like;

(4) as binders for protein coupling and fatty absorption in both tissue engineering and food industries;

(5) lubrication of joints and medical instruments;

(6) tissue coating and tissue protection from fibrosis, neurotoxins, inflammatory mediators, free radicals and other harmful materials;

(7) anti-adhesion compositions; and (8) as dermal fillers;

Useful properties include, but are not limited to bioadhesion, bioresorbability, antiadhesion, viscosity, and physical interpenetration.

Space Filling Materials

CPS/PO compositions of this disclosure can be particularly useful to fill voids in tissues resulting from disease or injury. For example, removal of a tumor during a surgical procedure can result in a loss of tissue volume. In situations in which organ or tissue function depends on the shape of the organ or tissue, CPS/PO compositions of this disclosure can be used to fill the void. Similarly, in injuries, such as excavating injuries in which tissue volume is lost, CPS/PO compositions of this invention can be used to fill those voids.

In other embodiments, space filling materials can be used to provide bulk in internal locations. For example, in situations where a void has been created as a result of removal of internal tissue (e.g., removal of a sebacious cyst, bullet wound, removal of a localized tumor), in an area not subject to large movements (e.g., the torso), an implant can be made having a desired shape and having a desired elasticity. Such space filling materials, made according to the principles of this invention, can be highly biocompatible, having long residence times in the body. Such materials can be made in any particularly desired shape. Thus, if the void is irregular, the surgeon can shape the implant to match the void. After making a surgical incision through the skin, the implant is inserted and the wound sutured. Alternatively, the surgeon can inject a composition comprising a gel having particles of CPS/PO material therein. After introduction into the void, the material can conform to the shape of the void, thereby providing a uniform appearing structure.

In still further embodiments, space-filling materials can be contained within a biocompatible sac. For example, one can insert a CPS/PO ionically cross-linked composition into the spine to provide support in situations where the nucleus of a vertebral disk has become damaged. By encasing CPS/PO compositions within a sac, the implanted material can resist compressive forces, and therefore can be used to avoid nerve pinching, a common cause of pain in subjects with degenerating disks.

In still further embodiments, CPS/PO materials of this disclosure can be dried to form membranes. As described in U.S. Pat. No. 5,906,997 (incorporated herein fully by reference), CPS/PO membranes can be made by preparing a CPS/PO composition, and then drying the composition.

Load-Bearing Materials

Additionally, in situations in which tissue volume is lost through degeneration or other causes, CPS/PO compositions of this disclosure can be used to decrease adverse effects of such tissue loss. In certain aspects, CPS/PO compositions of this disclosure can be used in load bearing capacities. For example, voids in the bone ("bone voids") of a vertebral body (e.g., caused by surgical removal of a tumor or degeneration of a vertebral disk nucleus) can result in pain, loss of sensation and/or loss of motion or function, due in some cases, to compression of spinal nerves. CPS/PO compositions can be made with varying degrees of ionic cross-linking, and in cases in which there is a high degree of cross-linking, the compositions can support increased loads. To make such compositions, the CPS can be used having a lower molecular weight, so that higher concentrations of CPS may be used resulting in more ether and carboxyl groups available for ionic cross-linking. Also, using POs having lower molecular weights, can increase the number of cross-links ("cross-link density") in the matrix. As the cross-link density increases, the ability of the matrix to support a load can increase. Thus, in certain aspects, highly-cross-linked CPS/PO compositions can be used as nucleus replacements or to fill other hone voids.

In certain of these embodiments, a CPS/PO composition can be placed in a biocompatible sac or bag within the intervertebral space, other bone void where the disk and/or disk nucleus was present, or in other locations where containment of the composition of this invention is desired. A bag can be made of a silicone-based polymer, such as Silastic™ or another, less deformable material, such as Mylar™ or other suitable material. It can be desirable to use a bag that has sufficient strength to resist breakage under the loads expected to be placed on the bag. Additionally, because both a CPS/PO composition and the wall tension (under Laplace's law) can resist a load, these embodiments can be used in situations in which relatively large loads are to be borne.

Thus, in some embodiments, a biologically compatible bag (which may have a "one-way" valve to permit introduction of material into the bag but won't permit unwanted loss of material) of an appropriate size to fit within the intervertebral space or other location can be inserted in a deflated condition. Such insertion can minimize trauma to the vertebral bodies and the annulus. Once inserted into place, a CPS/PO ionically cross-linked composition can be introduced into the bag using a needle. Once in the bag, the composition can act as a load-bearing structure, thereby replacing the lost or damaged nucleus. In embodiments in which there is frank loss of bone (e.g., due to removal of a tumor), a CPS/PO ionically cross-linked composition can be used to fill the void. Replacement CMC/PEO load bearing compositions generally can be surgically implanted. Alternatively, a biocompatible bag or sac can be inserted in a deflated condition as described above for nucleus replacement, and then filled with a CPS/PO composition, which can act as a load-bearing material.

One can also introduce CPS/PO mixtures into a sac or bag, and then introduce multivalent cations and multivalent organic anions into the sac. Upon mixing, the CPS, PO, cations and anions can react with each other, thereby forming the ionically cross-linked CPS/PO composition.

In some embodiments, multiple bags or sacs can be used. In particular, in situations in which high loads are to be expected (e.g., the knee, ankles or other lower extremities, or lower back), the use of multiple, small sacs can be employed to take advantage of the fact of the well-known Laplace relationship between transmural pressure, radius and wall stress of a closed sac. As used herein the term "transmural pressure" means the hydrostatic pressure inside the sac minus the hydrostatic pressure outside the sac. Thus, for a given transmural pressure, a sac having a smaller radius will have lower wall stress placed upon the sac. In contrast, a larger sac will have larger wall stress at the same transmural pressure because of the larger radius.

Based on the Laplace relationships (one for a sphere; $T=PR$ and another for a cylinder; $T=PR/2$), in certain embodiments of this disclosure, one can use a series of small, cylindrical sacs, each inserted into a bone void and filled with CPS/PO composition of this disclosure. It can be desirable to align the longitudinal axes of the small sacs in parallel with the expected load. Thus, during polymerization, the small sacs can support the load better than a single sac having larger radius.

Additionally, in situations in which the annulus is damaged, one can introduce one or more sacs in the intervertebral space, with one near the hole in the annulus. Thus, when filled, the sac near the hole in the annulus can effectively seal the hole and minimize further loss of intervertebral material. In other embodiments, smaller sacs can be inserted and filled (to support the load) and a larger "plug" sac can be introduced into the intervertebral space. If this plug sac is then inflated with a CPS/PO composition of this disclosure, the sac can effectively plug the hole in the annulus and thus prevent the smaller sacs from being extruded.

In additional aspects, CPS/PO compositions can be used to support loads within the skeletal system. For example, the spine is often a location where degeneration, injury or disease can produce loss of structural support. In particular, in conditions in which the disk is damaged, CPS/PO compositions of this invention can be readily used. In situations in which the nucleus pulposus is partially or completely lost, compositions of this invention can be used to replace the lost tissue. In some of these embodiments, an elastic, relatively non-compressible composition can be polymerized before insertion into the affected area. In other situations, one can administer a composition of this invention prior to its polymerization, so that the composition polymerizes in situ. For example, in situations in which there is frank loss of bone, producing an irregularly shaped defect, a mixture of components of this invention can be injected. After polymerization, the composition can fit well into the defect, thereby providing structural support.

In other situations, compositions of this invention can be placed within one or more bags or sacs. These embodiments can have increased load-bearing abilities, due to the facts that: (1) a composition can be supported against compression by the bag or sac, and/or (2) the composition has its own load-bearing abilities.

Vehicles for Controlled Delivery of Bioactive Substances

CPS/PO compositions of this disclosure can be used to deliver drugs, biologicals, nutrients or other biologically active agents (bioactive substances) to an animal. CPS/PO compositions can be made incorporating a bioactive substance therein to provide a controlled-release composition. In general, CPS/PO compositions having more cross-links tend to retain bioactive substances more than compositions having fewer cross-links. Such is the case for bioactive substances that are released from a CPS/PO composition by simple diffusion out of the matrix. In some cases in which the bioactive substance is large (e.g., protein), the bioactive substance may be released by a combination of simple diffusion out of the CPS/PO matrix and by release as the matrix is degraded in the body.

Regardless of which type of release occurs, it can be appreciated that the release of bioactive agents can be controlled as desired by varying the composition of the CPS/PO composition of this disclosure. It is not intended that the type of bioactive substance be limited. Rather, any bioactive substance whose release is desired to be controlled can be effectively delivered using CPS/PO compositions of this disclosure.

It can be readily appreciated that any number of drugs, biologicals and other chemical agents can be delivered using the CPS/PO composites of this disclosure.

It can also be appreciated that various hormones and steroids can be delivered, as can other, systemically acting drugs, which can be delivered transmucosally or transdermally. These include IgG, clotting factors and enzymes for treating mucopolysaccharidosis or other conditions.

Cardiovascular drugs include vasodilators such as β-adrenoreceptor agonists including terbutaline and low-dose epinephrine, α-adrenoreceptor antagonists including norepinephrine, high-dose epinephrine and the like, and vasodilators including nitroprusside and nitroglycerin.

Vehicles for Localized Release of Bioactive Substances

In situations in which local release of a bioactive substance is desired, a CPS/PO composition of this disclosure can be useful. Such situations may apply during tissue healing after surgery, where localized trauma to tissues produces localized inflammation. Thus, a CPS/PO composition of this disclosure may contain a vasoactive substance to control bleeding (e.g., a vasoconstrictor, such as norepinephrine) or to promote hemostasis (e.g., a clotting factor). CPS/PO compositions of this disclosure can also be useful for localized delivery of toxic agents in chemotherapy. For example, after tumor resection surgery, it may be desired to administer locally to the site, a CPS/PO composition having a chemotherapeutic agent incorporated therein. Such localized application may permit application of higher concentrations of anti-tumor medications at the site needed, while reducing systemic side effects of traditional intravenous injection.

Certain agents can be advantageously used for local delivery, providing desired concentration at a desired site, but while decreasing undesirable, systemic effects. Such agents include, but are not limited to therapeutic proteins, such as thrombin to aid in attaining and maintaining hemostasis, growth factors for bone, cartilage, skin and other tissue and cell types. Some of these peptide and protein growth factors include bone morphogenic protein (BMP), epidermal growth factor (EGF), connective tissue growth factor (CTGF), platelet derived growth factor (PDGF), angiotensin and related peptides, and RGD-containing peptides.

Additionally, locally acting drugs include fungicides, histamine, antihistamine, anti-inflammatory drugs (corticosteroids, methotrexate), local anesthetics, angiogenesis promoting drugs (e.g., to treat cardiovascular disease, and anti-angiogenesis factors (e.g., to treat tumors).

DNA-based therapeutics, including antisense DNA, gene therapeutics and RNA-based therapeutics are also suitably delivered using the compositions of this invention. These agents can be used to either inhibit or promote transcription of endogenous genes, or alternatively, can provide exogenous gene products to promote local treatment.

Locally delivered chemotherapeutic agents can also be delivered. These include, by way of example only, antibiotics to treat microbial conditions, antifungal agents, anti-parasitic agents, anti-neoplastic agents including alkylating agents, anti-metabolites and the like.

Binders for Protein Coupling

Other uses include more general uses of proteins, fats and other biological substances, whether bioactive or not. Thus, proteins can be incorporated into space filling CPS/PO compositions of this disclosure. Such proteins may include collagen, gelatin, of other proteins known in the art.

Lubricants

CPS/PO compositions of this disclosure can be effective lubricants for medical instruments. In situations in which a medical instrument is inserted into a body, there is a likelihood of at least some tissue trauma resulting. Trauma, even slight trauma, can cause tissue damage, and can result in unwanted effects. Such effects include bleeding, inflammation, adhesion formation or scarring. By coating a medical instrument with a CPS/PO composition of this disclosure prior to insertion into the body, such trauma can be decreased.

Lubrication can be used for both acute and chronic uses. Thus, for an acute procedure, such as urethral catherization, a CPS/PO composition of this disclosure can be used to decrease pain and other discomfort as well as ease insertion. By decreasing urethral trauma, use of CPS/PO compositions of this disclosure can decrease post-catheterization side effects, including decreasing pain on urination, urethral adhesions, and decreased likelihood of infection.

CPS/PO compositions of this disclosure can also be effective tissue lubricants. In situations in which tissues traumatize adjacent tissues (e.g., in joints), compositions of this invention can be used to decrease friction and thereby decrease localized trauma. Thus, by injecting a CPS/PO composition into an affected joint, pain can be reduced. By reducing friction and pain, the usual cascade of inflammation can be inhibited. By inhibiting inflammation, secondary adverse effects of inflammation can be decreased. Such adverse effects can be mediated by macrophages, leukocytes, mast cells, eosinophils, and mononuclear cells among others, each of which can produce bioactive substances that can make the situation worse. For example, mast cells contain potent proteases (e.g., mast cell tryptase and mast cell chymotryptase) that can degrade normal tissue proteins. Additionally, a series of interleukins can be released from neutrophils, macrophages and other inflammatory cells. Interleukins can be potent chemoattractive molecules and can recruit other inflammatory cells locally to the area, and can thereby continue adverse side effects of tissue trauma. Finally, tissue trauma can activate neuropeptide-containing nerves (e.g., c-fibers) known to contain substance P, which is a potent stimulus of pain pathways. In addition to causing pain, substance P is a potent chemoattractant and stimulator of mast cells.

In certain embodiments, CPS/PO compositions of this disclosure can be used to lubricate joints, such as those in the spine. In particular, CPS/PO compositions can be used to lubricate facet joints between adjacent lateral spinous processes. Similarly, compositions of this invention are useful as lubricants for other joints, including the knee, shoulder, elbows, wrists, ankles and hips.

Certain aspects of this disclosure include use of CPS/PO ionically cross-linked compositions to provide lubrication for other joints and soft tissues. In situations in which injury to bone, ligaments, tendons, fascia or other soft tissues has occurred, healing may not produce a smooth-functioning tissue. For example, damage to facet joints in the spine can result in abnormal alignment of vertebrae, which can lead to further damage to the disk (annulus or nucleus pulposus). Thus, a CPS/PO composition of this disclosure can be injected between lateral spinous processes of adjacent vertebrae (which normally can slide past one another during normal movement). After such injection, the lateral spinous processes can be separated from each other, and the inherent lubrication afforded by the CPS/PO composition can decrease further irritation.

In a similar fashion, damage to tendons, ligaments and fascias can produce pain, swelling and decreased function. This, insertion of a CPS/PO composition of this invention can improve mobility and can decrease the likelihood for further damage to the tissue.

Tissue Coatings: Antiadhersion Compositions

CPS/PO compositions of this disclosure have wide applicability as tissue coating agents. CPS/PO compositions can be used as anti-adhesion preparations. Adhesions are unwanted attachments of a tissue with an adjacent tissue. Adhesions commonly occur after surgery in which tissues are damaged as a result of the surgery. Thus, CPS/PO compositions of this disclosure can be effectively used to provide a physical barrier between tissues that would otherwise tend to adhere to each other. CPS/PO compositions may be membranes, gels or sponges. Many anti-adhesion uses are described in U.S. Pat. Nos. 5,096,997, 6,017,301, 6,034,140, 6,133,325, 6,566,345, 6,869,938 and 7,192,984, each patent expressly incorporated herein fully by reference as if individually so incorporated.

In still further embodiments, compositions of this invention can be used as antiadhesion materials. Methods for using CPS/PO compositions for antiadhesion purposes are described in U.S. Pat. Nos. 5,906,997, 6,017,301, 6,034,140, 6,133,325, 6,193,731, 6,869,938, and 7,192,984. Each of the aforementioned patents are expressly incorporated by reference as if separately so incorporated. It can be readily appreciated that gels, membranes and other forms of the CPS/PO compositions of this invention can be used in similar ways.

Additionally, CPS/PO compositions of this disclosure can be useful to minimize joint pain. In numerous conditions, including arthritis, traumatic injury, degeneration of cartilage, and ligament damage, a joint can become painful. A CPS/PO composition of this disclosure can be introduced into an affected joint to provide lubrication and to protect adjacent tissues from damage caused by movement. For example, in the knee, a CPS/PO composition can be introduced during an arthroscopic procedure. In situations in which the joint must bear a load (e.g., knee, hip, ankle, vertebra), a CPS/PO composition can be made with particularly high elasticity.

CPS/PO compositions can also be used to protect tissues from damage. For example, such compositions can protect peripheral nerves, tendons, ligaments, other soft tissues, synovial membranes, joints, and can thereby relieve pain.

For example, tendon and ligament injuries heal more slowly than to other tissues, in part because the blood flow to tendons and ligaments is reduced compared to tissues such as muscles, mesenteries, and the like. Furthermore, a tendon stress-related injury often is accompanied by a stress injury to an adjacent ligament. Therefore, healing of both tissues is required for a return to normal function. However, such recovery is often slow, and re-injury is common. Further, even when healed, tendons and ligaments tend to heal with scar tissue, which is not smooth. Thus, even after healing, a previously injured tendon or ligament may abrade adjacent tissues and cause either re-injury or slow recovery processes.

In another example, in the spinal cord, damaged spinous processes or vertebral bodies may abrade adjacent tissues. Additionally, loss of a vertebral nucleus can lead to compression of vertebral bodies and can result in impingement of spinal nerves, often leading to pain and/or paralysis.

A further example can involve damage to peripheral nerves, where soft tissue injury, trauma or inflammatory reactions can lead to pain or loss of nerve function. Application of a CPS/PO composition of this disclosure can decrease inflammatory responses, and therefore can decrease secondary damage caused by inflammatory reactions mediated by, for example, macrophages, leukocytes, mast cells or other types of inflammatory cells.

Dermal Fillers

Augmentation of the skin can be an important factor in recovering from injury or for cosmetic purposes. For example, with normal aging, skin may become loose or creases can form, such as nasal-labial (nasolabial) folds. In the face, creases or lines may adversely affect a person's self esteem or even a career. Thus, there has been a need for compositions and methods that can diminish the appearance of creases or lines.

Further, there are situations in which loss of tissue can leave an indentation in the skin. For example surgical removal of a dermal cyst, lipoatrophy or removal of a solid tumor can result in loss of tissue volume. In other cases, injuries, such as gunshot wounds, knife wounds, or other excavating injuries may leave an indentation in the skin. Regardless of the cause, it can be desirable to provide a dermal filler that can increase the volume of tissue to provide a smoother or more even appearance.

Several compositions are available for such purposes. Collagen is often used as an injectable material for soft tissue augmentation. Additionally, numerous other materials, including proteins, fats, hyaluronic acid (HA), polyalcohols, and other polymers have been used as injectable dermal fillers. However, non-cross linked, hydrophilic polymers such as collagen, gelatin and HA have not performed well and must be covalently cross-linked to remain in place to be effective. One example is ZYDERM®, which is uncrosslinked bovine collagen, was not effective as a dermal filler unless it was first cross-linked with glutaraldehyde to convert it to ZYPLAST®. Similarly, HA has not been sufficiently effective as a space filling material when injected or implanted in the body unless it is first cross-linked.

Compositions of CPS and modified CPS have unique properties that allow such compositions to be injected into the skin to fill spaces and to provide support where support is desired. One example for needed support is dermal augmentation in the face where dermal and subdermal volume is lost due to aging. CPSs including CMC have a unique property of being an elastic gel with unique physical properties such as dynamic, plastic and zero shear viscosity, tissue adhesiveness, cohesiveness and flow characteristics. In addition, it can achieve these properties without the requirement of covalent cross-linking. CPSs including CMC are particularly unique because chemical modifications of CMC increases the number of physical properties that make it an ideal injectable polymer for human treatment. For example, change in the degree of substitution has a dramatic effect on thixotropy and on viscosity of the gel. Its biocompatability and viscoelastic properties make it uniquely useful for injection into human skin where it becomes a space filling, biocompatible polymer.

Other polymers tested for their ability to perform as space filling gels are polysaccharides that have been used for soft tissue filing are inferior to CPSs. For example, HA must be cross-linked to cause it to function as an elastic gel. Cross-linking limits its ability to be injected through narrow gauge needles, because the cross-linking converts HA into particles. For example, RESTYLANE® is a product consisting of cross-linked HA in a compatible solution.

Proteins used for dermal augmentation, such as collagen, also must be cross-linked to perform well as dermal fillers. For example, ZYPLAST® is a cross-linked bovine collagen dermal filler.

CPSs can be a carrier for additional material for additional material for the skin, including hydrogel polymers such as PEO and emulsions. CPSs can be used to deliver drugs to the skin, such as antioxidants, retinol, vitamins and growth factors. Covalent cross-linking of polymers converts them into particles that diminish their ability to deliver additional polymers, liposomes, emulsions or other particulates.

Numerous substances have been tested over the years for augmenting soft tissue in the dermis in the face to improve cosmesis by filling depressions in the skin (Klein and Elson, *The History of Substances for Soft Tissue Augmentation*, Dermatological Surgery 26:1096-1105, 2000). This is an area that continues to be studied as there has been no clearly superior material or product (Hotta, *Dermal Fillers: The Next Generation*, Plastic Surgical Nursing 24(1):14-19, 2004). These fillers are prepared from several polymers including bovine collagen, porcine collagen, chicken or bacteria fermented HA, gelatin, all of which are cross-linked covalently to reduce their dissolution time or immunological reactions. Fillers also include autologous human collagen (cross-linked collagen from the patient), human cadaver dermis (cross-linked human collagen). Additional fillers are those that are insoluble in the dermis, including PMMA beads, dPTFE (expanded polytetrofluoroethylene), poly lactic acid, recombinant elastin, and thermoplastics that form gels when injected into humans (Klein and Elson, *The History of Substances for Soft Tissue Augmentation*, Dermatological Surgery 26:1096-1105, 2000). More recently, ceramic particles (U.S. Pat. No. 5,922,025) and also PMMA microspheres (Lemperle et al, *Migration Studies and Histology of Injectable Microspheres of Different Sizes in Mice*, Plast. Reconstr. Surg 113(5):1380-1390 (2004) have been used for soft tissue augmentation.

Dermal fillers are used to fill scars, depressions and wrinkles. Dermal filler substances have various inflammatory responses in the dermis including phagocytosis to foreign body reactions depending on the material (Lemperle et al., *Human Histology and Persistence of Various Injectable Filler Substances for Soft Tissue Augmentation*, Aesthetic Plast. Surg. 27(5):354-366; discussion 367 (2003). One goal of dermal fillers it to temporarily augment the dermis to correct the surface contour of the skin without producing an unacceptable inflammatory reaction, hypersensitivity reaction or foreign body reaction that causes pain, redness or excessive scar formation for a period of time.

One of the first materials to be used for dermal augmentation is ZYPLAST® derived form bovine collagen. A newer material used for this application is RESTYLANE® derived from bacteria-produced HA. Because challenges include both biocompatibility and persistence in the skin, new dermal fillers are compared to one of the existing products such as ZYPLAST® or RESTYLANE® (Narins et al., *A Randomized, Double-Blind, Multicenter Comparison of the Efficacy and Tolerability of Restylane Versus Zyplast for the Correction of Nasolabial Folds*, Dermatol. Surg. 29:588-595 (2003).

More recently, CMC has been used with polyethylene oxide (PEO) and multivalent ions to produce ionically linked materials (U.S. Pat. No. 7,192,984, incorporated herein fully by reference).

Compositions of this disclosure are particularly well suited as dermal fillers. As noted above, one of the difficulties with prior art dermal fillers is mismatching of the elasticities of the tissue and the dermal filler. In situations where the tissue is relatively elastic and the dermal filler is relatively inelastic, lumps can appear where the tissue can stretch, but the dermal filler does not. Conversely, in situations in which the elasticity of the dermal filler is higher than that of the tissue, incomplete filling of voids can occur.

Thus, by selecting viscoelastic properties of a dermal filler to approximate or match the elasticity of the tissue, a better void-filling material can be produced and used, while minimizing adverse effects of tissue-filler mismatching.

Additionally, as an individual ages, the elasticity of the skin tends to decrease. Thus, in subjects with less elastic skin, one might desirably use a dermal filler with lower elasticity than one might use in a younger individual with more elastic skin. Similarly, certain tissues tend to have different elasticities or different mobilities. For example, the skin around facial muscles (e.g., nasolabial folds) may be subject to different stresses than other tissues (e.g., the lips). Thus, one can select dermal fillers having different viscoelastic properties for use in the same subject.

Use of such dermal fillers depends upon the specific need. For example, when used to fill small wrinkles, such as nasolabial folds, or "crow's feet" around the eyes, dermal fillers in the form of a uniform gel or small particles can be desired. An advantage of using a uniform gel is that these materials can be injected using very small needles, and can produce a very smooth filling, particularly well suited for smoothing small lines. For use in somewhat larger lines (e.g., nasolabial folds), it can be desirable to use compositions comprising a gel having particles of CPS/PO. Such particles can be made according to methods known in the art, and can be made to have desired dimensions. For use in nasolabial folds, the particles should be sufficiently small to pass easily through a small needle (e.g., a 25 or 30 gauge needle). The remainder of the composition can be a CPS/PO gel having relatively lower viscosity. After injection, the particles can further hydrate in the tissue, thereby forming a more uniform composition.

General Methods

In the following section, manufacture of CPS/PO compositions are presented. However, it should be appreciated that CMC need not be the only CPS used. Rather, any CPS can be used in manufacture of CPS/PO compositions in similar fashions without departing from the scope of this invention.

Manufacture of CPS/PO Compositions

To manufacture CPS/PO (e.g., CMC/PEO) compositions of this disclosure, generally the CPS is dissolved in aqueous medium, such as water, saline, phosphate-buffered saline, physiologically compatible aqueous solvent solution or other suitable medium. For example, dissolving a CPS in aqueous media is generally accomplished by adding a pre-weighed amount of powdered, dry CPS into a vessel containing the medium with stirring, such as with a vortex mixer until the CPS is completely dissolved. In some embodiments, a CPS can be present in a concentration of from about 1% by weight to about 30% by weight. In other embodiments, CMC can be present in a concentration of about 3% weight per volume to about 15% by weight per volume. The molecular weights of CPS can be in the range of from about 50,000 D to about 1,000,000 D, alternatively from about 90 kD to about 700 kD.

To produce a CPS/PO composition, generally, preweighed amounts of CPS and PO are prepared, dissolved in an aqueous medium, containing a polyvalent cation (having a certain concentration) and a polyhydroxyl organic anion (having a certain concentration), with mixing, until the components are well mixed. The solution after mixing is generally steam sterilized to directly prepare a sterile composition for use. Thus, a CPS/PO ionically cross-linked composition can be prepared and drawn into a syringe, the syringe can then be sterilized (e.g., using steam). When the reaction has occurred, the resulting material can be instilled into a desired location through a small-gauge (e.g., 29 or 30 gauge) needle. In other embodiments, solutions of CPS and PO can be sterilized before mixing.

In some embodiments, the solution can be a physiologically compatible solution, with biocompatible pH, ionic strength, and colloid osmotic pressure.

In certain embodiments, NaCl can be used in a concentration in the range of about 0.001% by weight or weight/volume to about 10% by weight or weight/volume, and alternatively from about 0.01 to about 5.0%. In certain embodiments, isotonic saline can be used (e.g., about 0.9%).

A solution of multivalent cation (e.g., $CaCl_2*H_2O$) can be used in concentrations of from about 0.001% weight/volume to about 50% weight/volume and in alternatives, from about 0.01% to about 10%. In other embodiments, CPS/PO compositions can be made in phosphate buffered saline or other physiologically compatible medium.

Additionally, pH can be varied to produce compositions that have some hydrogen bonded components. Useful pH ranges can be in the range of about 6.0 to about 8.0. Adjusting pH can be accomplished by immersing a CMC/PEG composition in a buffer solution at the appropriate pH.

In other embodiments, CPS/PO compositions can be used precipitated and reconstituted in aqueous buffer solution.

Rheological Methods

Once a CPS/PO ionically cross-linked composition is prepared, its viscoelastic properties can be readily determined using equipment and methods known in the art. Small deformation oscillation measurements were carried out with a Thermo Haake RS300 Rheometer, Newington, N.H., in the cone and plate geometry. All measurements can be performed with a 35 mm/1° titanium cone sensor at 25° C. The elastic modulus, G', and loss modulus, G", were obtained over a frequency range of 0.628-198 rad/sec. Tan δ was calculated as G"/G'.

In some embodiments, the CPS can be sodium carboxymethylcellulose (CMC) obtained from Hercules and polyethylene oxide) was obtained from Sigma-Aldrich Corporation.

According to manufacturer, CMC A has an average Mn of ~700,000 Da and CMC B had a average Mn of ~200,000 Da. Rheological measurements were performed on gels prepared at 30 mg/ml solids concentration in BupH Modified Dulbecco's Phosphate Buffered Saline solution (PBS) purchased from Pierce Chemical (catalog No. 28374). The solutions can be prepared by stirring or CMC into the PBS at room temperature for at least two hours. The resultant solutions were clear and colorless with no solids evident and thus were used without filtration.

CPS/PO compositions can be sterilized using any conventional method, such as steam sterilization, irradiation or filtration.

Determination of Compressive Strength of CPS/PO Compositions

To determine the compressive strength of CPS/PO compositions, a suitably shaped piece of material (e.g, 1 inch×1 inch×0.25 inches) can be prepared and placed on a surface such as a table. Once polymerization has occurred, a load (e.g., a known weight) can be placed on the composition. The weights can be progressively increased until the composition fractures. Alternatively, a composition can be placed in a vise, with a pressure gauge inserted, and the load increased progressively until the composition fractures.

Sterilization of CPS/PO Compositions

As noted above, CPS/PO compositions may be conveniently sterilized using heat. In some embodiments, the composition may be heated in an autoclave or other steam producing apparatus. In some cases, it can be desirable to prepare a CPS/PO composition and then place it into a delivery device, such as a syringe. CPS/PO compositions can be made using a "3-step" process, in which: (1) a CPS/PO mixture is obtained, (2) multivalent cations and polyhydroxyl organic anions are added to start the cross-linking reaction and (3) where the cross-linked material is precipitated and reconstituted. Alternatively, a CPS/PO composition can be made using a "one-step" process, in which the CPS/PO solution is made with cations and anions and then placed in a delivery device for sterilization. After sterilization in situ, the CPS/PO composition is ready to use.

One-Step Delivery

It can be appreciated that certain embodiments (e.g., "one-step") embodiments can provide easy to produce, pre-sterilized compositions in a suitable delivery device (e.g., syringe). Pre-made CPS/PO compositions, having desirable elasticity, can be injected directly into the site using a small gauge (e.g. 25, 26, 27, 28, 29 or 30 gauge) needle.

In each of the above situations, CPS/PO compositions of this invention can be beneficial.

EXAMPLES

The following examples are presented to illustrate certain embodiments of this disclosure, and are not intended to limit the scope to the embodiments so illustrated. Rather, workers of skill in the art can modify or adapt the teachings of this invention to make and use other variations without undue experimentation. All of those embodiments are considered to be part of this disclosure.

Example 1. Preparation of CMC/PEO Gels in a $CaCl_2$/NaCl Salt Mixture: General Description To a 400 ml polypentene beaker, fitted with a mechanical stirrer, we added distilled, deionized water (DIW) (200 mL), $CaCl_2$ (see Table 1 for amounts), and NaCl (see Table 1 for amounts). After the salts were dissolved the solution was mixed at 700 rpm while a solid mixture of CMC A (6.66 g) and PEO A (0.74 g) were slowly added to the vortexing solution. After 5 minutes the stirrer was set to 145 rpm for 2 hours resulting in a clear viscous gel. The gel was filtered through a 100μ mesh filter under pressure and loaded into 20 mL polypropylene syringes. The syringes were loaded into autoclavable sterilization pouches and steam sterilized. After sterilization the gel was set at room temperature overnight before measuring the viscosity, osmolality, and pH. Table 1 below presents results of this experiment. "Visc" means viscosity, and "OSMO" means osmolality. Results are shown in Table 1 below.

TABLE 1

Properties of CMC/PEO Gels made with $CaCl_2$ and NaCl

| | | | Post Sterilized Values | | |
|---|---|---|---|---|---|
| Gel Number | [$CaCl_2$]mM | [NaCl]mM | Visc | OSMO | pH |
| Gel 1-3 | 33 | 69 | 268 | 275 | 6.16 |
| Gel 1-2 | 16 | 99 | 364 | 315 | 6.26 |
| Gel 1-1 | 8 | 99 | 431 | 280 | 6.35 |

Example 2. Preparation of a CMC/PEO Gel in a Calcium Gluconate/NaCl Salt Mixture: General Description To a 400 ml polypentene beaker, fitted with a mechanical stirrer, we added distilled, deionized water (DIW) (200 mL), calcium gluconate (see Table 2 for amounts), and NaCl (see Table 2 for amounts). After the salts were dissolved the solution was mixed at 700 rpm while a solid mixture of CMC A (6.66 g) and PEO A (0.74 g) were slowly added to the vortexing solution. After 5 minutes the stirrer was set to 145 rpm for 2 hours resulting in a clear viscous gel. The gel was filtered through a 100μ mesh filter under pressure and loaded into 20 mL polypropylene syringes. The syringes were loaded into autoclavable sterilization pouches and steam sterilized. After sterilization the gel was set at room temperature overnight before measuring the viscosity, osmolality, and pH. After sterilization the gel was set at room temperature overnight before measuring the viscosity, osmolality, and pH. Table 2 below presents results of this experiment. "Visc" means viscosity, "OSMO" means osmolality, and "CaClu" means calcium gluconate.

TABLE 2

Properties of CMC/PEO Gels made with CaGluconate and NaCl

| | | | Post Sterilized Values | | |
|---|---|---|---|---|---|
| Gel Number | [CaGlu] | [NaCl] | Visc | OSMO | pH |
| 2-3 | 33 | 69 | 925 | 296 | 6.37 |
| 2-2 | 16 | 99 | 884 | 314 | 6.41 |
| 1-2 1-1? | 8 | 99 | 642 | 284 | 6.42 |

Viscosities of the post-sterilized compositions of Examples 1 and 2 are depicted in FIG. 2.

As shown in Table 1 and FIG. 2, the viscosity of compositions of this disclosure are very different from those of the prior art. Results of the experiments in Example 1 show notable properties. First, with increasing calcium concentration, the viscosity of $CaCl_2$-containing materials decreases. Such behavior is characteristic of compositions of CPS and PO ionically cross-linked with $CaCl_2$. This property is shared by the compositions disclosed by Schwartz et al. (U.S. Pat. No. 6,869,938).

In contrast to the observed decrease in viscosity with increasing calcium ion concentration, compositions of the instant disclosure exhibited two properties shown in Example 2. First, as shown in FIG. 2, at the same calcium ion concentration, the viscosity of calcium gluconate-containing compositions is higher that for compositions ionically cross-linked using $CaCl_2$. Second, and most surprisingly, with increasing calcium ion concentration, the viscosity of calcium gluconate-containing compositions increases, so that the viscosity of the gluconate-containing compositions is substantially higher than the viscosity of compositions cross-linked using $CaCl_2$ (or calcium ions, per se).

These effects represent a result that is completely unexpected based on the prior art. These effects represent an advantageous and excellent effect, and render compositions of the instant disclosure highly suitable for the uses to which such compositions can be used. For example, using the disclosures herein, it is possible to produce a composition having a desired viscosity without using increased amounts of CPS or PO. Because CPS and PO are eliminated according to physiological processes, one may be able to use a high-viscosity material that does not overburden the physiological processes, and in some cases, may permit a shorter residence time in the body. Such a feature may be particularly useful in acute situations in which the residence time of the composition need not be long.

Example 3. Preparation of a CMC/PEO Gels in a CaCl$_2$/NaCl Salt Mixture

General Description

To a 400 ml polypentene beaker, fitted with a mechanical stirrer, we added distilled, deionized water (DIW) (200 mL), CaCl$_2$ (see Table 3 for amounts), and NaCl (see Table 3 for amounts). After the salts were dissolved the solution was mixed at 700 rpm while a solid mixture of CMC A (7.21 g) and PEO A (0.19 g) were added to the vortexing solution. After 5 minutes the stirrer was set to 145 rpm for 2 hours resulting in a clear viscous gel. The gel was filtered through a 100μ mesh filter under pressure and loaded into 20 mL polypropylene syringes. The syringes were loaded into autoclavable sterilization pouches and steam sterilized. After sterilization the gel was set at room temperature overnight before measuring the viscosity, osmolality, and pH. Results are shown in Table 3 below.

TABLE 3

Properties of CMC/PEO Gels made with CaCl$_2$ and NaCl. Post Sterilized Values

| Gel Number | [CaCl$_2$]mM | [NaCl]mM | Visc | OSMO | pH |
|---|---|---|---|---|---|
| Gel 3-3 | 33 | 69 | 294 | 280 | 6.55 |
| Gel 3-2 | 16 | 99 | 393 | 310 | 6.60 |
| Gel 3-1 | 8 | 99 | 461 | 295 | 6.57 |

Example 4. Preparation of CMC/PEO Gels in a Calcium Gluconate/NaCl Salt Mixture General Description To a 400 ml polypentene beaker, fitted with a mechanical stirrer, we added distilled, deionized water (DIW) (200 mL), calcium gluconate (see Table 4 for amounts), and NaCl (see Table 4 for amounts). After the salts were dissolved the solution was mixed at 700 rpm while a solid mixture of CMC A (7.21 g) and PEO B (0.19 g) were slowly added to the vortexing solution. After 5 minutes the stirrer was set to 145 rpm for 2 hours resulting in a clear viscous gel. The gel was filtered through a 100μ mesh filter under pressure and loaded into 20 mL polypropylene syringes. The syringes were loaded into autoclavable sterilization pouches and steam sterilized. After sterilization the gel was set at room temperature overnight before measuring the viscosity, osmolality, and pH. After sterilization the gel was set at room temperature overnight before measuring the viscosity, osmolality, and pH. Results are shown in Table 4 below.

TABLE 4

Properties of CMC/PEO Gels made with CaGluconate and NaCl. Post Sterilized Values

| Gel Number | [CaGlu] mM | [NaCl] mM | Visc | OSMO | pH |
|---|---|---|---|---|---|
| 4-3 | 33 | 69 | 1015 | 298 | 6.77 |
| 4-2 | 16 | 99 | 948 | 310 | 6.60 |
| 4-1 | 8 | 99 | 705 | 295 | 6.66 |

It can be readily appreciated that the presence of gluconate substantially increased the viscosity of gels containing this polyhydroxyl anion.

Example 5. Preparation of CMC/PEO Gels in a Sodium Gluconate/NaCl Salt Mixture: General Description To a 400 ml polypentene beaker, fitted with a mechanical stirrer, we added distilled, deionized water (DIW) (200 mL), sodium gluconate (see Table 5 for amounts), and NaCl (see Table 5 for amounts). After the salts were dissolved the solution was mixed at 700 rpm while a solid mixture of CMC A (6.66 g) and PEO A (0.74 g) were slowly added to the vortexing solution. After 5 minutes the stirrer was set to 145 rpm for 2 hours resulting in a clear viscous gel. The gel was filtered through a 100μ mesh filter under pressure and loaded into 20 mL polypropylene syringes. The syringes were loaded into autoclavable sterilization pouches and steam sterilized. After sterilization the gel was set at room temperature overnight before measuring the viscosity, osmolality, and pH. After sterilization the gel was set at room temperature overnight before measuring the viscosity, osmolality, and pH. Results are shown in Table 5 below.

TABLE 5

Properties of CMC/PEO Gels made with NaGluconate and NaCl Post Sterilized Values

| Gel Number | [NaGlu] mM | [NaCl] mM | Visc | OSMO | pH |
|---|---|---|---|---|---|
| 5-3 | 33 | 69 | 1003 | 300 | 6.55 |
| 5-2 | 16 | 99 | 861 | 312 | 6.52 |
| 5-1 | 8 | 99 | 700 | 296 | 6.57 |

It can be readily appreciated that the effect of gluconate to increase viscosity of CPS/PO gels is not dependent on the cation present in the mixture. Thus, sodium gluconate (Table 5) and calcium gluconate (Table 4) show similar increases in viscosity.

Example 6. Preparation of CMC/PEO Gels in a Sodium Gluconate/NaCl Salt Mixture: General Description To a 400 ml polypentene beaker, fitted with a mechanical stirrer, we added distilled, deionized water (DIW) (200 mL), sodium gluconate (see Table 6 for amounts), and NaCl (sec Table 6 for amounts). After the salts were dissolved the solution was mixed at 700 rpm while a solid mixture of CMC A (7.21 g) and PEO B (0.19 g) were slowly added to the vortexing solution. After 5 minutes the stirrer was set to 145 rpm for 2 hours resulting in a clear viscous gel. The gel was filtered through a 100μ mesh filter under pressure and loaded into 20 mL polypropylene syringes. The syringes were loaded into autoclavable sterilization pouches and steam sterilized. After sterilization the gel was set at room temperature overnight before measuring the viscosity, osmolality, and pH. After sterilization the gel was set at room temperature overnight before measuring the viscosity, osmolality, and pH. Results are shown in Table 6 below.

TABLE 6

Properties of CMC/PEO Gels in a Sodium Gluconate/NaCl Salt Mixture Post Sterilized Values

| Gel Number | [NaGlu] mM | [NaCl] mM | Visc | OSMO | pH |
|---|---|---|---|---|---|
| 6-3 | 33 | 69 | 1010 | 315 | 6.65 |
| 6-2 | 16 | 99 | 870 | 300 | 6.61 |
| 6-1 | 8 | 99 | 725 | 299 | 6.657 |

I claim:
1. A composition, comprising:
a carboxypolysaccharide (CPS), said CPS being hyaluronic acid (HA), a polyalkylene oxide (PO), said CPS and said PO ionically cross-linked using a poly- hydroxyl organic anion (PHA), to form a biocompatible membrane, bead, particulate, coating, gel, or physiologically compatible aqueous solution.

2. The composition of claim 1, said PO being polyethylene oxide (PEO).

3. The composition of claim 1, said PHA being gluconate.

4. The composition of claim 1, further comprising a cation.

5. The composition of claim 4, said cation being calcium ($Ca^{+2}$).

6. The composition of claim 4, said cation being sodium (Na+).

7. The composition of claim 1, said PO having an average molecular weight of between about 5000 Daltons and about 8000 Daltons.

8. The composition of claim 1, said composition having a ratio of HA, PO, and PHA to said physiologically compatible aqueous medium being in the range of about 1% by weight solids to total solution to about 30% by weight solids to total solution.

9. A method, comprising providing components:
a hyaluronic acid (HA),
a PO,
a PHA, and
an aqueous solution; and
dissolving said HA, PO, and PHA in said aqueous solution, thereby forming an ionically cross-linked composition.

10. The method of claim 8, further comprising a cation.

11. The method of claim 9, said cation being calcium ($Ca^{+2}$).

12. The method of claim 10, said cation being sodium (Na+).

13. The method of claim 8, further comprising sterilizing said composition.

14. A method, comprising:
providing a composition of claim 1; and
inserting said composition into a portion of a body in need thereof, where said need is for one or more of anti-adhesion, tissue lubrication, lubrication of an instrument, and space-filling.

15. The method of claim 14, said composition comprising HA, PEO A, gluconate, and an aqueous medium.

16. The method of claim 15, said aqueous solution being a physiologically compatible medium.

* * * * *